US005584886A

United States Patent [19]
Lai

[11] Patent Number: 5,584,886
[45] Date of Patent: Dec. 17, 1996

[54] MAXILLOFACIAL PROSTHETIC MATERIALS

[76] Inventor: Juey H. Lai, 14617 White Oak Dr., Burnsville, Minn. 55337

[21] Appl. No.: 420,205

[22] Filed: Apr. 11, 1995

[51] Int. Cl.$^6$ ....................................................... A61F 2/02
[52] U.S. Cl. .................................. 623/11; 623/6; 623/8; 523/113; 523/115
[58] Field of Search .................................. 623/4, 6, 8, 11, 623/15; 523/113, 115

[56] References Cited

U.S. PATENT DOCUMENTS

| | | | |
|---|---|---|---|
| 4,208,506 | 6/1980 | Deichert et al. | 528/32 |
| 4,647,282 | 3/1987 | Fedorov et al. | 623/4 |
| 4,832,978 | 5/1989 | Lesser | 623/15 |
| 5,137,448 | 8/1992 | Dougherty et al. | 433/214 |
| 5,268,396 | 12/1993 | Lai . | |
| 5,387,105 | 2/1995 | Dougherty et al. | 433/214 |

OTHER PUBLICATIONS

Tsai, F. H., Xiao, C., Koran, A., and Yee, A. F., "Synthesis of Silicone Block Copolymers for Use as Maxillofacial Materials", *Transactions of the Acxademy of Dental Materials*, vol. 5, No. 1, Feb. 14, 1992, pp. 124–125.

Antonucci, Joseph, "Polymers and Elastomers for Extra–Oral Maxillofacial Prosthetics", *Transactions of the Academy of Dental Materials*, vol. 5, No. 1, Feb. 14, 1992, pp. 136–137.

*Primary Examiner*—Paul B. Prebilic
*Attorney, Agent, or Firm*—Haugen and Nikolai, P.A.

[57] ABSTRACT

A maxillofacial prosthetic material is disclosed with a composition based on the methacrylic siloxane resin methacryloxypropyl-terminated polydimethylsiloxane (MPDS) in combination with an amount of filler material, an amount of thermally activated initiator and an amount of crosslinking agent together with an amount of coloring pigment and UV stabilizer added to and dispersed in the polymer prior to cure.

22 Claims, No Drawings

MAXILLOFACIAL PROSTHETIC MATERIALS

This invention was made with Government support under Grant No. 1R43DE11076-01 awarded by the National Institute of Health. The Government has certain rights in the invention.

BACKGROUND OF THE INVENTION

1. Field of the Invention

The present invention relates generally to adhesively applied external prosthetic materials for the human body and, more particularly, to improved materials for use in maxillofacial reconstructive prostheses for application to correct facial defects. The materials are characterized by improved adherence, tear strength and color retention qualities.

2. Related Art

Maxillofacial prosthetic materials are materials externally applied to correct facial defects resulting from cancer surgery, accidents, congenital deformities or the like. The major requirements for the materials include high resiliency, high tear resistance and tensile strength, adequate softness, miscibility with the colorants, compatibility with adhesive material and facial tissues, and the materials must be non-toxic and non-irritating.

Several plastic materials, including acrylic polymers, silicones and polyurethanes, have been used for maxillofacial reconstruction. Among them, polysiloxanes, or the so-called silicones, have been used most widely. This is mainly due to several generally favorable qualities including ease of fabrication, high degree of chemical inertness, low degree of toxicity, and high degree of thermal and oxidative stability. The uniqueness of polysiloxanes is that siloxane bonds Si—O—Si in the main chains, as well as Si—C bonds where side groups are bonded to silicon, are extremely flexible and have a great freedom of motion. This is reflected in their lower viscosity, lower surface tension, lower melting point and glass transition temperatures, and is responsible for the elastomeric behaviors of many polysiloxanes.

Some discussion of the chemistry of silicone elastomers should be helpful in understanding the invention. In general, to be useful polysiloxanes must be cross-linked to form solid elastomer materials. Cross-linking of polysiloxanes can be achieved by any of the following process mechanisms:

1. Free radical cross-linking of linear polysiloxanes through the use of organic peroxides, e.g. benzoyl peroxide, at elevated temperature. The method is applicable to both polysiloxanes with unreactive end groups and polysiloxanes with reactive group, e.g. vinyl groups. The resulting materials are known as heat-vulcanized (HTV) silicones, 2. Cross-linking of linear polysiloxane with reactive end groups such as silanols (hydroxyl-terminated polysiloxanes). This method of crosslinking requires a crosslinking agent, e.g. tetraethyl silicate, and a catalyst, e.g. dibutyl tin dilaurate, and is a condensation reaction by nature.

3. Cross-linking of polysiloxanes by addition reactions. The reactions involve the addition of silyl hydride groups (—SiH) to vinyl groups ($CH_2$=CH—) attached to silicon with the aid of a platinum containing catalyst.

The silicone elastomers themselves, including those that have been used for maxillofacial reconstruction, are generally classified into two types according to the crosslinking process, namely, heat-vulcanized (HTV) silicones and room temperature-vulcanized (RTV) silicones.

As indicated above, HTV silicones are polydimethylvinylsiloxane copolymers which have at least a small percentage of vinyl groups in the side chains of the polymers. The copolymer undergoes crosslinking according to the mechanism 1 as described above. Crosslinking occurs at the vinyl groups at high temperature (>100° C.) with the aid of a thermal initiator, e.g. benzoyl peroxide, which acts as the free-radical polymerization and crosslinking initiator. Heat decomposes the initiator into free radicals which initiate the crosslinking of the polymer molecules and convert the linear polymer into a resilient elastomer. The heat activated crosslinking reaction is in the nature of an additional reaction which does not produce any by-product.

Two types of RTV silicones have been used. The first type is produced by the crosslinking of hydroxyl-terminated polydimethylsiloxanes (I) as in mechanism 2 above.

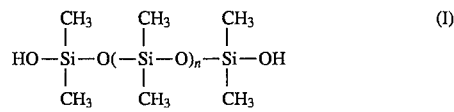

where n is an integer having a value from 1 to about 10,000.

The crosslinking is a condensation reaction by nature, and requires a crosslinking agent. In Medical Adhesive Type A (Dow Corning), methyl triacetoxy silane (II) is used as the crosslinking agent.

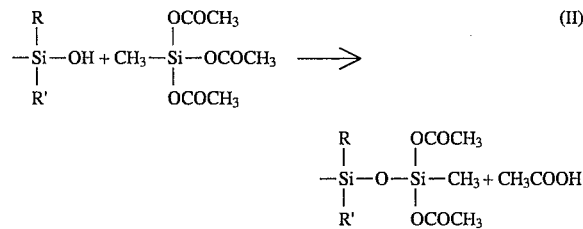

The crosslinking, however, requires water molecules to hydrolyze the silane and as seen in (II), produces acetic acid (an irritant) as the by-product. Since Medical Adhesive Type A requires moisture to cure at room temperature, the cure time is excessively long making it impractical for curing the material inside a mold. The use of Medical Adhesive Type A has therefore been limited to that of an extrinsic colorant carrier applied to the surface of the prosthesis. Further, the siloxane bonds formed by the condensation reaction are susceptible to degradation reactions such as hydrolysis. The prostheses have relatively low tear strength and are incapable of maintaining edge resistance.

The second type of RTV silicone involves the crosslinking of polysiloxanes by addition reactions. The reactions generally involve the addition of silyl hydride groups (—SiH) to vinyl groups ($CH_2$=CH—) attached to the silicone with the aid of a platinum containing catalyst (III) as in mechanism 3, above.

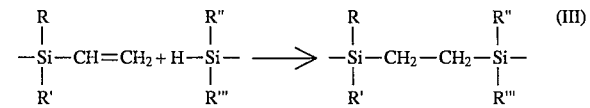

where R, R', R" and R''' groups are alkyl groups (almost exclusively methyl groups).

The second type of RTV silicones are not truly RTV silicones. The curing of these silicones, in fact, requires heating the material at 150° C. for a time, possibly an hour.

Although these materials have improved tear strength over the first type of RTV silicones, they are also very hydrophobic. Generally, these materials have low adhesion to non-silicone-based adhesives, and do not readily accept extrinsic coloration. Further, the cure of the materials may be inhibited by traces of amines, sulfur, nitrogen oxides and organo-tin compounds.

The current siloxane maxillofacial materials are generally RTV silicones which are supplied as two parts. As soon as the catalyst and the crosslinker are mixed, the curing reactions start immediately. Therefore, the working time for these materials is rather limited. This is especially troublesome when de-airing of the mixture requires more than 30 minutes of vacuum pumping. In addition, the catalysts have a rather short shelf life (6 months). Furthermore, since the cure of the materials can be inhibited by traces of various impurities, use of pigments and colorants free of the impurities is required to prevent the cure inhibition. This severely limits the choice of colorants.

Polysiloxane materials including acryloxy- and methacryloxyalkyl-terminated polydimethylsiloxanes (MPDS) of the following general schematic structural formula:

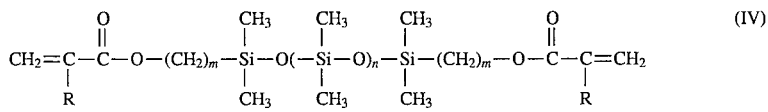

where m is an integer having a value from 1 to about 6, where n is an integer having a value from 1 to about 10,000, and where R is H or $CH_3$, have been proposed for an internal use, namely, as the primary constituent material for a soft denture liner as disclosed in U.S. Pat. No. 5,268,396 issued to Juey H. Lai, the inventor in the present application. That document is deemed incorporated herein by reference for any and all purposes.

Thus, although a number of polysiloxane-based maxillofacial prosthetic materials are currently available and are at least partially successful, current polysiloxane-based maxillofacial prosthetic materials are still far from ideal. Major problems associated with the current prosthetic materials include degradation of physical properties, discoloration of the prostheses, and the difficulty of repairing.

Despite the progress that has been made in the area of maxillofacial prostheses, there remains a need to provide a siloxane maxillofacial material of the low temperature HTV type that exhibit or retains high tear strength but which readily accepts extrinsic coloration, is less hydrophobic and which, once formulated and mixed, has an increased working or open time and a long shelf life.

Accordingly, it is a primary object of the invention to provide an improved maxillofacial prosthetic material having improved properties.

Another object of the invention is to provide a maxillofacial prosthetic material having improved facial adherence properties.

Yet another object of the invention is to provide a maxillofacial prosthetic material having improved physical characteristics.

A further object of the present invention is to provide a maxillofacial prosthetic material having improved color retention qualities.

A still further object of the invention is to provide a maxillofacial prosthetic material of the low temperature HTV silicone type which afford an indefinite open or working time prior to cure.

A yet still further object of the present invention is to provide a maxillofacial prosthetic material having an extended shelf life.

Other objects and advantages of the invention will become apparent to those skilled in the art upon familiarization with the specification including the examples in the claims of this application.

SUMMARY OF THE INVENTION

By means of the present invention, improved maxillofacial prosthetic materials are provided of compositions based on the siloxane resin: acryloxyalkyl or methacryloxyalkyl terminated polydimethylsiloxane (MPDS) (IV).

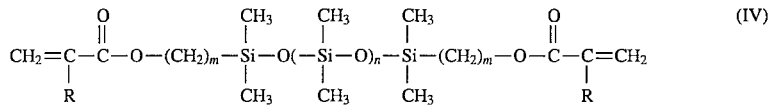

where m is an integer having a value from 1 to about 6, where n is an integer having a value from 1 to about 10,000, and where R is H or $CH_3$.

The proposed materials of the invention do not have the shortcomings of prior silicone materials. The MPDS will not cure unless it is heated to a temperature above 50° C., thus it has a very long working time. The shelf life of MPDS can be extended to more than a year by adding a small amount of polymerization inhibitor commonly added to commercial monomers. The most preferred material is methacryloxypropyl terminated polydimethylsiloxane in which R=$CH_3$ and m=3 in the above formula.

The prosthetic materials further include an amount of thermally activated (low temperature) initiator an amount of filler material and optionally (but preferably) an amount of crosslinking agent. The initiator is preferably selected from free radical initiators including benzoyl peroxide and lauroyl peroxide with the latter being preferred. The preferred filler material is selected from quartz, amorphous silica and barium glass with amorphous silica, particularly amorphous silica coated with a silane coupling agent such as hexamethyldisilazane being most preferred. The amount of initiator is generally less than 1% of the weight of the composite material and that of the filler may constitute up to 40% or more of the material. Preferred crosslinking agents include tri(ethylene glycol) dimethacrylate (TEGDMA), bis(3-methacryloxypropyl) tetramethyl disiloxane (MPTD) and ethylene glycol dimethacrylate (EGDMA) with TEGDMA in an amount of about 10% of the mixture or less and between 1% and 6% being most preferred.

The desirable properties of the polymer MPDS are due to a unique chemical structure. The crosslinkable polysiloxane provides the silicone elastomer characteristics. The dimethacrylate groups located on the chain ends readily undergo free-radical thermal polymerization and crosslinking at temperatures below 100° C. The polymer, unlike prior silicone maxillofacial prosthetic materials, of the most preferred materials possesses methacrylic characteristics due to the presence of the methacrylate groups.

The methacrylic characteristic of certain of the polymers may be enhanced by the incorporation of a dimethacrylate monomer, e.g., tri(ethylene glycol) dimethacrylate, as the crosslinking agent and so such a material is generally preferred. Furthermore, the reactions involving MPDS and dimethacrylate crosslinking agents are free-radical addition polymerizations and are crosslinking in nature. These crosslinked bonds, unlike those produced by the condensation reactions (above), are more stable and more resistant to degradation reactions. The substantial amount of methacrylate groups in the polymer network increases tear strength, bonding strength to adhesives and miscibility with desirable colorants.

There are many advantages associated with the prosthetic materials based on polysiloxane MPDS (IV) over previous silicone prosthetic materials. The materials can be processed at a low temperature. MPDS possesses dimethacrylate groups which readily undergo free-radical polymerization and crosslinking upon application of low heat, light or chemicals. The curing of the polysiloxane MPDS can be accomplished either by photo-crosslinking using a visible light photoinitiator and an activator, or by thermal crosslinking with the aid of an organic peroxide at temperatures as low as 60° C.

The viscosity of polysiloxane MPDS available from Huls America is a suitable 2,000 cps. If desired, the viscosity of the material can be conveniently increased by adding a suitable amount of filler so that it remains low enough to facilitate the molding, yet high enough to retard the settling of suspended colorants.

As previously indicated, the required properties of maxillofacial prosthetic materials include high resiliency, high tear resistance and tensile strength, adequate softness, miscibility with the colorants, compatibility with the adhesive and facial tissues, and, of course, the materials must be non-toxic and non-irritants.

The material should exhibit good bonding to conventional maxillofacial prosthetic adhesives. Two kind of adhesives are currently used for maxillofacial prosthetic materials, namely, acrylics-based and silicone-based. As MPDS is a silicone polymer which possesses methacrylate groups which are chemically identical to those in polymethyl methacrylate (PMMA), the adhesion of the material to both the acrylic-based and silicone-based adhesives is excellent.

The material exhibits good miscibility with colorants as it is less hydrophobic and more polar than previous RTV and HTV prosthesis silicone materials. The material is better than current HTV and RTV silicone in accepting both intrinsic and extrinsic coloration.

DETAILED DESCRIPTION

The maxillofacial prosthetic materials of the invention possess the important requirements for successful prostheses. The viscosity of the material of the invention is in the range 10,000 and 75,000 cps, i.e., low enough to facilitate the molding, yet high enough to retard the settling of suspended colorants. The curing temperature (lower than 100° C.) allows use of a stone mold. Realistic long-term coloration of external facial prosthesis is also an important feature which increases patient satisfaction and acceptability. Both intrinsic and extrinsic colorants, e.g., pigments, are dispersible in the prosthetic materials.

The tear strength of the materials is preferably in the range, 30 to 100 ppi (53 to 175 N/cm), so that they are capable to resist rupture at edge for daily use. The prostheses must also be relatively strong. The required tensile strength is in the range 300 to 1,000 psi (2.0 to 7 MPa). The prostheses must also be soft having a hardness of less than about 40 and preferably in the range 25–35 Shore A scale and resilient enough to respond to facial motion. The required modulus at 100% elongation is in the range 50 to 250 psi (0.5 to 1.7 MPa). The materials should also possess low glass transition temperature in order to prevent the stiffening of material when exposed to cold temperatures.

Adequate adhesion of the material to the facial tissue by means of a compatible adhesive is also an important requirement. The material must be wettable by the adhesive used. Since maxillofacial materials may come in direct contact with facial tissue, the materials should be non-toxic and non-irritating to the user. Low water sorption and water solubility are also important considerations. The prostheses should not distort when boiled in water or sterilized in steam.

In accordance with previous work including certain examples, formulations of the maxillofacial materials were studied as functions of cure temperature, initiator concentration, filler concentration, the nature of the crosslinkers and the concentration of the crosslinker using statistical experimental design. The materials were evaluated in terms of hardness, ultimate elongation, tensile strength, tear strength, and peel strength to adhesives. The dispersibility of pigments with maxillofacial materials was studied. Color stability of the maxillofacial materials with and without pigments and UV stabilizers was also investigated.

The maxillofacial materials based on MPDS have been found to be very promising indeed. Compared with the current maxillofacial materials used as controls MDX4-4210 (Dow Corning Corporation) and A-2186 (NuSil Technology), MPDS is about a factor of 2 higher in tear strength. The peel strength, which is the characterization of the bonding strength to the adhesives is more than 40% higher than that of MDX4-4210. The hardness of MPDS is similar to that of MDX4-4210. The tensile strength of MPDS is higher, and the ultimate elongation is slightly lower than that of MDX4-4210.

Unpigmented MPDS did not exhibit perceptible color change after exposure to UV light for 24 hours. Three pigments, red, yellow and suntan were individually added to MPDS as the intrinsic colorants. Among the three, only the red pigmented MPDS showed faint discoloration after exposure to UV light for 24 hours. Incorporation of a UV stabilizer into the red pigmented MPDS, however, was successful in removing the perceptible color change associated with the UV exposure.

Thermal curing of the polysiloxane MPDS was conducted in a stainless steel mold to minimize the effects of oxygen inhibition. First, a thermal initiator was dispersed in the polymer MPDS; and thereafter filler powders were added to the mixture and mixed thoroughly. After de-airing by a vacuum pump, a crosslinker was added and blended into the mixture. The mixture was then introduced to the mold and cured.

Methacryloxypropyl-terminated polydimethylsiloxane polymer starting material was obtained from United Chemical Technology, Inc. A GPC (gel permeation chromatography) analysis of the polymer indicated that the polymer has the following molecular weights: Mn (number-average molecular weight)=9,100, $M_w$ (weight average molecular weight)=39,900, and dispersity=$M_w/M_n$=4.4.

Two organic peroxides, benzoyl peroxide and lauroyl peroxide, were tested as the free radical thermal initiator for cure. Lauroyl peroxide was found to be more miscible with MPDS and dispersed easier in the polymer than benzoyl peroxide. Lauroyl peroxide has since been used as the preferred thermal initiator.

A number of inorganic fillers, including quartz, amorphous silica, and barium glass, were considered as preferred fillers for the polymer to enhance the mechanical properties and ease of handling of the polymer. Among these, amorphous silica is considered to be most suitable and so is most preferred. Amorphous silica is available in a wide range of particle sizes and also has a refractive index of 1.460 which closely matches the refractive index of 1.416 for the polymer MPDS.

Four amorphous silica fillers, F-01(0.04 μm), F-02(0.016 μm), F-04(8.8 μm), and F-05(7.0 μm) were tested. Three silane coupling agents, γ-methacryloxypropyltrimethoxysilane (CA-01), vinyl triethoxysilane (CA-02), and hexamethyldisilazane (CA-03) were applied individually to the fillers and evaluated. Incorporation of Filler F-02, which has an average particle size of 0.016 μm and is coated with the silane CA-03, hexamethyldisilazane, has produced MPDS (cured) with higher tensile strength and higher ultimate elongation than the others and so is the preferred filler for MPDS.

Three high molecular weight dimethacrylate monomers were evaluated as the crosslinking agents for MPDS. They were tri(ethylene glycol) dimethacrylate (TEGDMA) (XA-01), Bis(3-methacryloxypropyl)tetramethyldisiloxane (MPTD) (XA-02), and ethylene glycol dimethacrylate (EGDMA) (XA-03). Several tests were conducted to determine the physical and mechanical properties of MPDS as a function of the crosslinking agents used. Hardness, ultimate elongation, and tensile strength of the cured MPDS which contained 1.5% of each of the crosslinkers were determined as functions of two filler concentrations, 10 and 20%. In both cases, the elastomers which contained the crosslinker XA-01, TEGDMA, consistently had higher tensile strength and ultimate elongation than the others. Thus, the crosslinker XA-01, TEGDMA, is the preferred crosslinking agent for MPDS.

Chemical, physical and mechanical properties of the MPDS maxillofacial materials have also been found to depend on the degree of crosslinking, the amount of crosslinking agent and the filler in the polymer network. The degree of crosslinking depends on the nature and the concentration of the thermal initiator and the crosslinking agent used, and the curing conditions such as cure temperature and cure time. For a given thermal initiator, filler, and crosslinking agent, thermal initiator concentration, filler concentration, XAC (crosslinker concentration), cure temperature, and cure time have been found to be important considerations in determining properties of the prosthetic materials.

A two-level fractional factorial experimental design matrix using Design-Ease software (Stat-Ease, Inc., Minneapolis, Minn.) was first performed to identify the important factors which affect the material properties. The experimental design is shown in Table 1 using tests 1–8. Each test represents a single run. The formula of each test was cured at 65° C. for 16 hours.

TABLE 1

Two-level Fractional Factorial Design for Maxillofacial Material Formulation
($2^{4-1}$ = 8 runs)

| Test No. | Formulation No. | HMAC (%) | Crosslinker (%) | LPOC (%) | Filler (%) | Hardness | Elongation | Tensile Strength (MPa) |
|---|---|---|---|---|---|---|---|---|
| 1 | MF-21 | 0 | 0 | 0.2 | 10 | 13 | 171 | 0.15 |
| 2 | MF-22 | 1.5 | 0 | 0.2 | 20 | 18 | 209 | 0.36 |
| 3 | MF-23 | 0 | 1.5 | 0.2 | 20 | 19 | 225 | 0.35 |
|   | MF-24 | 1.5 | 1.5 | 0.2 | 10 | 18 | 204 | 0.32 |
| 5 | MF-25 | 0 | 0 | 0.4 | 20 | 16 | 277 | 0.50 |
| 6 | MF-26 | 1.5 | 0 | 0.4 | 10 | 16 | 143 | 0.21 |
| 7 | MF-27 | 0 | 1.5 | 0.4 | 10 | 18 | 245 | 0.35 |
| 8 | MF-28 | 1.5 | 1.5 | 0.4 | 20 | 25 | 248 | 0.52 |
|   | Mean value |   |   |   |   | 17.8 | 215 | 0.34 |

In tests 1–8, the four variables were an additional monomer species n-hexyl methacrylate concentration (HMAC), crosslinking agent concentration, lauroyl peroxide thermal initiator concentration (LPOC), and filler concentration. Two different concentrations of each variable were used, i.e., 0 or 1.5% for HMAC, 0 or 1.5% for crosslinker concentration, 0.2 or 0.4% for LPOC, and 10 or 20% for filler concentration.

Hardness, ultimate elongation, and tensile strength of the cured MPDS were determined as functions of the variables. The monomer, n-hexyl methacrylate was added to see if MPDS could be benefited from its presence. Experimental results were analyzed using Design-Ease software. The main effects of the variables are shown in Table 2. No significant interaction was found for the four variables.

TABLE 2

Calculated Effects from Fractional Factorial Design

| Variable | Range (%) Low | Range (%) High | Hardness | % Elongation | Tensile Strength (MPa) |
|---|---|---|---|---|---|
| HMAC | 0 | 1.5 | 2.6 | −29.8 | 0.01 |
| Cross-linker | 0 | 1.5 | 4.1 | 30.0 | 0.09 |
| LPOC | 0.2 | 0.4 | 1.9 | 26.0 | 0.10 |
| Filler | 10 | 20 | 3.4 | 49.0 | 0.18 |

Tests 1–8 and Table 2 indicate the following:

a. The addition of HMAC apparently was of no benefit. On the contrary, % elongation of MPDS was decreased significantly (29.8%) by the addition of 1.5% HMAC to the polymer. Some increase in hardness was observed.

b. The addition of 1.5% of crosslinking agent significantly increases hardness (4.1), elongation (by 30%), and tensile strength (by 0.09 MPa).

c. It appeared that 0.2% of LPO is not sufficient to cure MPDS; increasing the LPOC to 0.4% has the effect of increasing the elongation by 26.0% and tensile strength by 0.10 MPa.

d. Among the four variables, filler concentration appeared to produce the largest effect. An increase in filler concentration from 10 to 20% increased the elongation by 49%, tensile strength by 0.18 MPa and hardness by 3.4.

The addition of crosslinker, and an increase in LPOC and filler concentration produced better elastomers. Another set of Examples (8–16) was produced to investigate the effects of increasing the concentrations of crosslinker, LPO and filler further.

Results of this two-level experimental design are reproduced in Table 3. Two different conditions are: 3.0 or 6.0% for XAC, 0.4 or 0.8% for LPOC and 20 or 30% for the filler concentration. As in tests 1–8, the formulated MPDS were all cured at 65° C. for 16 hrs. Hardness, % elongation and tensile strength were measured for each formulation.

TABLE 4

Calculated Main Effects and Interaction Effects from Two-level Factorial Design

| Variable | Range (%) Low | Range (%) High | Hardness | % Elongation | Tensile Strength (MPa) |
|---|---|---|---|---|---|
| A: XAC | 3.0 | 6.0 | 6.25 | −55.0 | 0.06 |
| B: LPOC | 0.4 | 0.8 | 1.75 | 12.8 | 0.21 |
| C: Filler | 20 | 30 | 5.75 | 199.8 | 1.44 |
| AB | | | −0.75 | −13.3 | −0.03 |
| AC | | | 1.25 | −50.3 | −0.18 |

The most significant findings from Table 4 are:

a. A significant increase in crosslinker (XAC) from 3.0% to 6.0% significantly increased the hardness (by 3.6), however, % elongation decreased by 55%.

b. The effect of an increase in LPOC from 0.4% to 0.8% was seen to be moderate on both hardness (1.75) and elongation (12.8%), but it increased the tensile strength noticeably (0.21 Mpa). It is contemplated that a range of 0.2 to 1.0% will be effective.

c. The effect of an increase in filler concentration from 20 to 30% again had the most pronounced effects. While a substantial increase in hardness (5.75) was observed, increases in both elongation (199.8%) and tensile strength (1.44 MPa) were the most significant.

These findings suggest that when MPDS is cured at 65° C. for 16.0 Hrs., properties are improved in formulae in which the crosslinker concentration=3.0%, LPOC =0.4 or 0.8%, and filler concentration=30.0% as in Examples 15 (MF-51) and 13 (MF-53).

Further increases in filler concentration might be useful; however, the fact that hardness of both Examples 15 and 13 are higher than 38 suggests that any significant increase in filler concentration will produce MPDS whose hardness is too high to be useful as maxillofacial prosthetic materials.

Both cure temperature and cure time affect the properties of the cured elastomers. A cure time of 16 hrs. has been

TABLE 3

Two-levels Factorial Design for MF Material Formulation* ($2^3 = 8$ runs)

| Test No. | Formulation No. | Cross-linker (%) | LPOC (%) | Filler (%) | Hardness | Elongation (%) | Tensile Strength (MPa) |
|---|---|---|---|---|---|---|---|
| 9 | MF-39 | 3.0 | 0.4 | 20 | 34 | 250 (33) | 0.88 (0.11) |
| 10 | MF-48 | 6.0 | 0.4 | 20 | 39 | 251 (24) | 1.14 (0.06) |
| 11 | MF-46 | 3.0 | 0.8 | 20 | 36 | 295 (31) | 1.17 (0.16) |
| 12 | MF-49 | 6.0 | 0.8 | 20 | 41 | 284 | 1.40 |
| 13 | MF-53 | 3.0 | 0.4 | 30 | 38 | 519 (42) | 2.55 (0.22) |
| 14 | MF-54 | 6.0 | 0.4 | 30 | 47 | 434 | 2.48 |
| 15 | MF-51 | 3.0 | 0.8 | 30 | 41 | 526 (13) | 2.73 (0.14) |
| 16 | MF-55 | 6.0 | 0.8 | 30 | 47 | 400 | 2.57 |
| | Mean value | | | | 40.4 | 369.9 | 1.86 |

*One run for each formulation only where a standard deviation is not shown in parentheses.

The results were analyzed using Design-Ease software. The calculated main effects and interaction effects are shown in Table 4.

adopted for ease of experimentation and removal of residual lauroyl peroxide remaining in the polymer. However, a wide range of cure times and temperatures are contemplated within the scope of the invention. Thus, temperatures between about 55° C. and 100° C. and times from about 4 hours and 24 hours.

Further studies of the effects of crosslinking agent concentration and cure temperature were also performed. Three cure temperatures, 65°, 78°, and 90° C. were selected. Since the crosslinking agent concentration affects tear strength, bonding strength to the adhesives, as well as tensile strength, hardness, and elongation, crosslinking agent concentration was varied from 0 to 6.0%.

Both LPOC and filler concentration were kept at near optimum levels, namely 0.8% and 30.0% respectively. Hardness, elongation, tensile strength, tear strength, and bonding strength to two adhesives, Secure Medical and Hydrobond, were measured. These results are shown in Table 5.

were made, and the data represent the mean value of the measurements.

The tensile strength and the ultimate elongation (elongation at break) of the materials were determined by using a Comten Tensile Tester (Model 922 MTT-20/02) according to ASTM Designation: D 412-92. In this method, test specimens in the general shape of dumbbells were molded by heat curing the samples in a 3-pieces stainless steel mold specifically designed and constructed for the measurement. Care was exercised to prevent the trapping of air bubbles in

TABLE 5

Properties of MPDS Maxillofacial Prosthetic Materials

| Cure Cond. | MF | Cross-linker (%) | Hardness | Elongation (%) | Tensile Strength (MPa) | Tear Energy (N/cm) | Peel Strength (N/cm) Secure | Peel Strength (N/cm) Hydrobond |
|---|---|---|---|---|---|---|---|---|
| 65° C. 16 hours | MF-62 | 0 | 26 | 676 (18) | 2.68 (0.04) | 227 (34) | 4.78 (0.28) | |
| | MF-64 | 0.5 | 32 | 611 (3) | 2.44 (0.13) | | | |
| | MF-65 | 1.0 | 34 | 628 (21) | 2.70 (0.19) | 320 (67) | 5.11 (0.25) | 0.96 (0.35) |
| | MF-59 | 1.5 | 37 | 548 (41) | 2.41 (0.13) | | | |
| | MF-66 | 2.0 | 39 | 518 (3) | 2.39 (0.06) | 315 (93) | 5.92 (1.00) | 1.96 (0.82) |
| | MF-51 | 3.0 | 41 | 526 (13) | 2.73 (0.14) | 347 (30) | | |
| | MF-55 | 6.0 | 47 | 400 | 2.57 | | 6.71 (0.95) | |
| 78° C. 16 hours | MF-62 | 0 | 24 | ≧730 | ≧2.56 149 | (4) | | |
| | MF-64 | 0.5 | 30 | 725 (19) | 2.80 (0.19) | 412 (102) | | |
| | MF-65 | 1.0 | 30 | 726 (19) | 2.66 (0.04) | 505 (67) | 5.04 (0.47) | |
| | MF-59 | 1.5 | 30 | 732 (4) | 2.39 (0.06) | | | |
| | MF-66 | 2.0 | 35 | 641 (13) | | | | |
| | MF-51 | 3.0 | 41 | 545 (54) | 2.56 (0.26) | 438 (71) | 5.92 (1.00) | 1.96 (0.82) |
| | MF-55 | 6.0 | 47 | 478 (20) | 2.74 (0.09) | | | 6.11 (0.91) |
| 90° C. 16 hours | MF-62 | 0 | 12 | 588 (37) | 0.85 (0.16) | 8 (1) | | |
| | MF-64 | 0.5 | 24 | ≧730 | ≧2.05 | | | |
| | MF-65 | 1.0 | 27 | ≧730 | ≧2.45 | 356 (64) | 4.59 (0.21) | |
| | MF-59 | 1.5 | 25 | ≧703 (8) | ≧1.55 (0.40) | | | |
| | MF-66 | 2.0 | 28 | 717 (14) | 2.13 (0.03) | 409 (116) | | |
| | MF-51 | 3.0 | 34 | 659 (41) | 2.46 (0.04) | 409 (26) | 4.24 (0.37) | 1.59 (0.82) |
| | MF-55 | 6.0 | 42 | 517 (6) | 2.52 (0.15) | 435 (44) | 6.34 (0.28) | |
| Control | A-2186 | | 25 | 717 (16) | 2.44 (0.09) | 191 (30) | 4.19 (1.00) | 0.67 (0.74) |
| | MDX4-4210 | | 30 | 800 (30) | 2.19 (0.14) | 200 (82) | 3.29 (0.28) | 0.77 (0.28) |

Evaluation of Maxillofacial Prosthetic Materials

The mechanical properties of the new prosthetic materials based on MPDS, including indentation hardness, tensile strength, elongation at break (ultimate elongation), tear strength, and bonding strength to the adhesives were determined as functions of the formulations. In addition, the dispersibility of pigments with the materials was investigated to determine the feasibility of intrinsic and extrinsic coloration of the materials. UV color stability of the pigmented MPDS was studied with and without UV stabilizers. The properties of the materials prepared under different formulations were determined to define the optimum formulations, and compared with those of two commercial prosthetic materials, MDX4-4210 and A-2186 (see Table 5). For MPDS formulations, a minimum of three specimens per test were used for each formulation. As for the controls, MDX4-4210 and A-2186, five specimens were used for each test.

The indentation hardness of the prosthetic materials was determined using a Shore A Durometer according to ASTM Designation: D 2240-86. A 3-piece stainless steel mold was constructed for preparing the test specimens. The dimension of each specimen was 1.5 in (diameter)×0.25 in (thickness). The hardnesses of the materials were determined immediately after cure. For each formulation, three specimens or more were measured. Five measurements of hardness at different positions on the specimens at least 0.26 inch apart the specimen. The thickness of the specimen was 2.5 mm, and the dimension of the connecting neck was 3.0 cm×2.0 cm. The test specimens were conditioned at 23° C. and 50% RH for 24 hrs prior to testing. The specimens were clamped between grips which were pulled apart at 2.0 in (5 cm)/min. The force at break was recorded, and from which tensile strength was calculated. The % elongation was=100× $(L-L_o)/L_o$ where L and $L_o$ represented the observed distance between bench mark at break and the original distance between bench marks.

Tear propagation resistance of the maxillofacial prosthetic films was evaluated according to ASTM designation D 1938-92. Test specimens were of the standardized trouser shaped strips having a dimension of 75 mm×25 mm×1 mm with a 50 mm long cut. The specimens were molded by heat curing in a 2-piece stainless steel mold, and were conditioned at 23° C. and 50% RH for 40 hrs. or more prior to testing. The testing machine was an Instron Tester (model 1122) using the software TestWorks for Windows v 3.0 (Sintech, a division of MTS Systems Corporation). The grip separation rate was 25 cm/min. Since the films were highly extensible, both the peak load (force) and the elongation at break (torn through) were recorded and used to calculate the tear energy according the equation $T=F(\lambda_T+1)/h$, where T=tear energy per unit area of torn surface, F=force required to tear the material, h=thickness of specimen, and $\lambda_T$ ratio of stretched leg length to unstretched leg length.

The bonding of adhesives to MPDS films was characterized by the peel test. Two popular adhesives, Dow corning 355 Medical Adhesive and Hydrobond (Daro Products, Inc., Butler, Wis.) obtained from Factor II, Inc. of Lakeside, Ariz., were used. The former is also called Secure Medical Adhesive and is a pressure sensitive adhesive widely used for adhering maxillofacial prosthetic devices. The latter is an acrylic type latex adhesive and is said to retain bonding even in the presence of water. The peel test method is that of ASTM: D 903-93. The specimen dimension is 3" (7.5 cm)×1.0" (2.5 cm)×⅛" (3 mm) with a 1 in$^2$ area bonded by the adhesive. The specimen was placed in the Instron Tester with the unattached prosthetic material tab bent back to a peeling angle of 180°. The specimen was then subjected to a peeling force by separation at 12 in. (30.5 cm)/min. until failure occurred. The force-per-unit-width of bond necessary to cause failure was determined for different formulations, and the failure cause examined. Because the film was relatively thick (3 mm), there was no significant stretching of the film during the peel test.

Coloration

Coloration of maxillofacial prosthetic material is generally achieved by intrinsic and/or extrinsic coloration. Intrinsic coloration is obtained by incorporating suitable pigments into the polymer before cure. To achieve this, the pigments must be dispersible in the polymer. In extrinsic coloration, the adhesive, such as Dow Corning Siliastic Medical Adhesive Type A, is diluted with a solvent such as xylene. Pigments are then added and mixed, and the colored adhesive is applied topically to the surface of the intrinsically colored prosthetic device and allowed to cure. Of course, the adhesive must bond well to the maxillofacial materials.

Four pigments of different colors were obtained from Factor II, Inc. They are monastral red (dark red), cosmetic red, cosmetic yellow ocher, and cosmetic suntan pigments. A small amount of each pigment, 0.02% of total weight, was added to the polymer paste and mixed thoroughly before cure. It was found that the pigments were all dispersed well in the polymer. The addition of the pigments did not have any significant effect on the mechanical properties of the materials. The mechanical properties of both pigmented and unpigmented materials are shown in Table 6.

TABLE 6

Effects of Pigment on the Cure

| MF All cured 90° C., 16 hours | Pigment Color | Concentration (0%) | Hardness | % Elongation | Tensile Strength (MPa) |
|---|---|---|---|---|---|
| MF-51-4 | | | 34 | 659 (41) | 2.46 (0.04) |
| MF-51-15 | Red | 0.02 | 33 | 656 (50) | 2.45 (0.10) |
| MF-51-14 | Suntan | 0.02 | 33 | 625 (55) | 2.34 (0.13) |
| MF-51-19 | Yellow | 0.02 | 30 | 750 | 2.48 |

To evaluate extrinsic coloring the adhesion of pigmented Medical Adhesive Type A was cured onto the surface of two MPDS films, and the adhesive strength was characterized by the peel test as described above. The adhesive strength of the Medical Adhesive Type A used as the extrinsic colorant carrier on MPDS and the controls was determined and is shown in Table 7.

TABLE 7

Bonding Strength of Maxillofacial Prosthetic Materials to Medical Adhesive Type A

| MF Material | Cure Condition | Bonding Strength (Peel N/cm) |
|---|---|---|
| MF-51 | 65° C., 16 hours | 9.54 (0.96) |
| A-2186 | 126° C., 70 min | 9.44 (0.14) |
| MDX4-4210 | 90° C., 2 hours + room temp 24 hours | 11.40 (0.89) |

A major deficiency of known prosthetic materials is their color instability. Color stability of the polysiloxane MPDS has been determined by the accelerated test similar to that of ADA specification No. 27. The siloxane elastomers were exposed to RS lamp (1700±100 µw/cm$^2$) for 24 hrs. Color change was rated by three persons and classified as: zero=no perceptible change, 1=barely perceptible, 2=perceptible, and 3=very perceptible. Color stability results are shown in Table 8.

Certain uv absorbers and antioxidants have been used in the chemical industry to enhance the color stability of polymers and organic materials. In this work, a uv stabilizer, 2-hydroxy-4-methoxybenzophenone (ST-1), and an antioxidant, butylated hydroxytoluene (AO-1), were used to enhance the color stability of red pigmented MPDS. While AO-1 was found to be not effective, ST-1 was found effective in minimizing the color change of the red pigment associated with uv exposure (see Table 8).

TABLE 8

Color Stability of MF Materials

| Material | Cure Condition | Pigment | Additive UV Stabilizer | Color Change |
|---|---|---|---|---|
| MF-66-6 | 90° C., 16 hours | none | none | 0 |
| MF-51 | 90° C., 16 hours | Suntan | | 0 |
| | 90° C., 16 hours | Yellow | | 0 |
| | 90° C., 16 hours | Red (cosmetic) | | 2 |
| | 90° C., 16 hours | Red (cosmetic) | AO-01 | 2 |
| | 90° C., 16 hours | Red (cosmetic) | ST-01 | 1 |
| | 90° C., 16 hours | Red (monastral) | | 1 |
| | 90° C., 16 hours | Red (monastral) | ST-01 | 0 |
| Medical Adhesive Type A | 23° C., 60 hours | Suntan | | 0 |
| | | Yellow | | 0 |
| | | Red (monastral) | | 0 |

With the exception of the run where an organic red pigment was used, all other pigmented MPDS and Medical Adhesive Type A did not show perceptible color change after exposure to the UV lamp at 37° C. for 24 hours.

New maxillofacial prosthetic materials based on MPDS with and without the crosslinking agent without TEGDMA were systematically formulated and evaluated using statistical experimental design. Two commercial silicone prosthetic materials, MDX4-4210 and A-2186 were used as the controls for comparison. The properties of the materials are shown in Table 5 for three groups of materials cured at three different temperatures.

Table 5 shows that the materials which were cured at 78° C. or 90° C. generally have better properties than those cured at 65° C. Within each temperature group, hardness, tear strength and adhesive bonding strength are seen to be increased with an increase in crosslinker concentration. While tensile strength of the materials is not significantly affected by the increase, ultimate elongation is seen to be decreased with the increase in crosslinker concentration.

At low concentration ranges, as the concentration of crosslinker increases, the degree of crosslinking is likely to be increased. An increase in the degree of crosslinking, in turn, results in an increase in hardness and tear strength accompanied by a decrease in ultimate elongation. Higher bonding strength of MPDS to the adhesives, Secure Medical and Hydrobond, associated with an increase in the TEGDMA concentration is attributed to an increase in the number of methacrylate groups in the polymer network which renders them less hydrophobic. Based on the results shown, the optimum formulation is most probably in the following range: Crosslinker concentration=2.0–6.0%, LPOC=0.4–0.8%, Filler concentration=30% to 40%, cure temperature=78°–90° C. and cure time=16 hours or less (yet to be optimized). The formulation MF-51 cured at 78° C. or 90° C. produced MPDS which have significantly higher tear strength (a factor of 2) and bonding strength to adhesives (40–100%) than those of the controls.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A heat curable maxillofacial prosthetic material comprising:
   (a) an amount of one or more polysiloxanes selected from the group consisting of acryloxyalkyl and methacryloxyalkyl-terminated polydimethylsiloxane having the structural formula

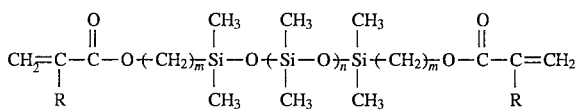

where m is an integer having a value from 1 to about 6, where n is an integer having a value from 1 to about 10,000 and where R is H or $CH_3$;
   (b) an amount of tri(ethylene glycol) dimethacrylate (TEGDMA) crosslinking agent wherein the amount of said crosslinking agent is about 10 percent or less based on the weight of the prosthetic material;
   (c) an amount of lauroyl peroxide initiator;
   (d) an amount of amorphous silica filler material, said filler material being coated with a silane coupling agent; and
   (e) an amount of coloring pigment dispersed in said polysiloxane material.

2. The maxillofacial prosthetic material of claim 1 wherein the siloxane coupling agent comprises hexamethyldisilazane.

3. The maxillofacial prosthetic material of claim 1 wherein the amount of filler material is from about 10 percent to about 40 percent by weight based on the weight of the prosthetic material.

4. The maxillofacial prosthetic material of claim 2 wherein the amount of filler material is from about 10 percent to about 40 percent by weight based on the weight of the prosthetic material.

5. The maxillofacial prosthetic material of claim 1 wherein the amount of said lauroyl peroxide is from about 0.2 percent to 1.0 percent based upon the weight of the prosthetic material.

6. The maxillofacial prosthetic material of claim 1 further comprising an amount of UV stabilizer.

7. The maxillofacial prosthetic material of claim 6 wherein said UV stabilizer includes 2-hydorxy-4-methoxybenzophenone.

8. A heat curable maxillofacial prosthetic material comprising:
   (a) an amount of one or more polysiloxanes selected from the group consisting of acryloxyalkyl and methacryloxyalkyl-terminated polydimethylsiloxane having the structural formula

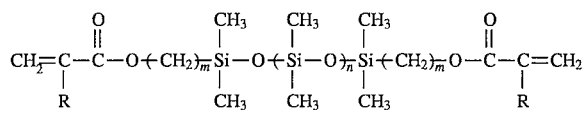

where m is an integer having a value from 1 to about 6, where n is an integer having a value from 1 to about 10,000 and where R is H or $CH_3$;
   (b) an amount of crosslinking agent selected from the group consisting of tri(ethylene glycol) dimethacrylate (TEGDMA) and ethylene glycol dimethacrylate (EGDMA);
   (c) an amount of lauroyl peroxide initiator; and
   (d) an amount of filler material selected from the group consisting of quartz, amorphous silica and barium glass.

9. The maxillofacial prosthetic material of claim 8 further comprising an amount of coloring pigment added to and dispersed in said polysiloxane material.

10. The maxillofacial prosthetic material of claim 8 wherein the crosslinking agent is TEGDMA and the amount of said crosslinking agent is less than about 10 percent based on the weight of the prosthetic material.

11. The maxillofacial prosthetic material of claim 8 wherein said filler material is amorphous silica coated with a silane coupling agent.

12. The maxillofacial prosthetic material of claim 11 wherein the siloxane coupling agent comprises hexamethyldisilazane.

13. The maxillofacial prosthetic material of claim 8 wherein the amount of said lauroyl peroxide is from about 0.2 percent to 1.0 percent based upon the weight of the prosthetic material.

14. The maxillofacial prosthetic material of claim 8 further comprising an amount of UV stabilizer.

15. The maxillofacial prosthetic material of claim 14 wherein said UV stabilizer includes 2-hydorxy-4-methoxybenzophenone.

16. A heat curable maxillofacial prosthetic material comprising:
   (a) an amount of one or more polysiloxanes selected from methacryloxypropyl-terminated polydimethylsiloxane having the structural formula

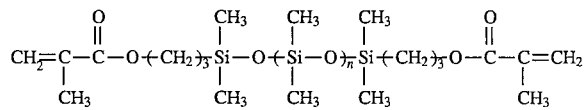

where n is an integer having a value from 1 to about 10,000;
   (b) an amount of tri(ethylene glycol) dimethacrylate (TEGDMA) crosslinking agent wherein the amount of said crosslinking agent is about 10 percent or less based on the weight of the material;

(c) an amount of lauroyl peroxide initiator;
(d) an amount of amorphous silica filler material, said filler material being coated with a silane coupling agent; and
(e) an amount of coloring pigment dispersed in said polysiloxane material.

17. The maxillofacial prosthetic material of claim 16 wherein the siloxane coupling agent comprises hexamethyldisilazane.

18. The maxillofacial prosthetic material of claim 16 wherein the amount of filler material is from about 10 percent to about 40 percent by weight based on the weight of the prosthetic material.

19. The maxillofacial prosthetic material of claim 17 wherein the amount of filler material is from about 10 percent to about 40 percent by weight based on the weight of the prosthetic material.

20. The maxillofacial prosthetic material of claim 16 wherein the amount of said lauroyl peroxide is from about 0.2 percent to 1.0 percent based upon the weight of the prosthetic material.

21. The maxillofacial prosthetic material of claim 16 further comprising an amount of UV stabilizer.

22. The maxillofacial prosthetic material of claim 21 wherein said UV stabilizer includes 2-hydorxy-4-methoxybenzophenone.

\* \* \* \* \*